Figure 1:
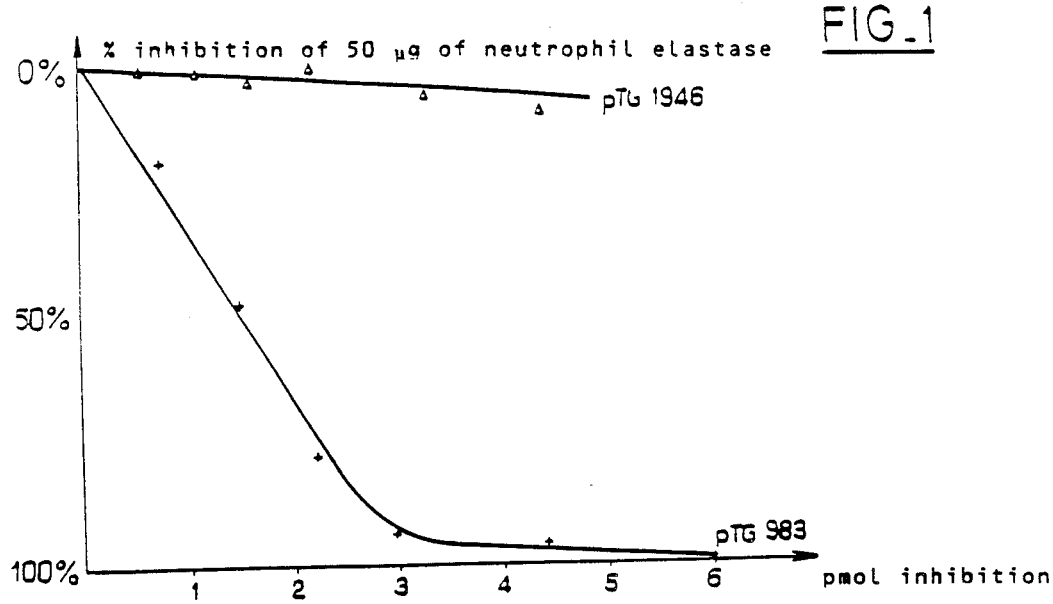

| United States Patent [19] | [11] Patent Number: 4,973,668 |
|---|---|
| Jallat et al. | [45] Date of Patent: Nov. 27, 1990 |

[54] VARIANTS OF ALPHA 1-ANTITRYPSIN WHICH ARE USEFUL, IN PARTICULAR, AS KALLIKREIN INHIBITORS

[75] Inventors: Sophie Jallat, Strasbourg; Michael J. Courtney, Brumath, both of France

[73] Assignee: Transgene S.A., Courbevoie, France

[21] Appl. No.: 60,346

[22] Filed: Jun. 10, 1987

[30] Foreign Application Priority Data

Jun. 10, 1986 [FR] France ................................ 86 08386

[51] Int. Cl.$^5$ ............................................ C07K 13/00
[52] U.S. Cl. ................................... 530/380; 530/350; 514/12; 424/94.64
[58] Field of Search ............................. 530/380, 350; 424/94.64

[56] References Cited

FOREIGN PATENT DOCUMENTS

| 0107278 | 5/1984 | European Pat. Off. . |
|---|---|---|
| 0155188 | 9/1985 | European Pat. Off. . |
| 0164719 | 12/1985 | European Pat. Off. . |
| 0169114 | 1/1986 | European Pat. Off. . |
| 0195592 | 9/1986 | European Pat. Off. . |
| 0200421 | 12/1986 | European Pat. Off. . |
| 8606408 | 11/1986 | PCT Int'l Appl. . |
| WO86/00337 | 1/1986 | World Int. Prop. O. .......... 530/380 |

OTHER PUBLICATIONS

Shapira, M. et al., Chem. Abs. 104:125616c, Apr. 1986.
Davis, A. et al., Proc. Natl. Acad. Sci., U.S.A., 83, 3161–3165, May 1986.
European Search Report, Aug. 26, 1987, EP 87 40 1400.
Expression, Purification and Characterization of Recombinant γ-Carboxylated Factor IX Synthesized in Chinese Hamster Ovary Cells, The Journal of Biological Chemistry, vol. 261, No. 21, 7/25, pp. 9622–9268, 1986.
6048 Nucleic Acids Research, vol. 15, No. 3, 1987, Oxford, England, pp. 871–884.
Expression of Active Human Factor IX in Transfected Cells, Nature, vol. 316, 18 Jul. 1985, pp. 271–273.
Active γ-Carboxylated Human Factor IX Expressed Using Recombinant DNA Techniques, vol. 316, Jul. 1985, No. 6025, pp. 268–270 Nature.
French Search Report, Apr. 17, 1987, FR 86 08 386.
Chemical Abstracts, vol. 102, No. 15, Apr. 15, 1985, p. 470.
Synthesis in E. Coli of $\alpha_1$-Antitrypsin Variants of Therapeutic Potential for Emphysema and Thrombosis, Nature, vol. 313, No. 5998, Jan. 10, 1985, pp. 149–151.
Mutation of Antitrypsin to Antithrombin, The New England Journal of Medicine, vol. 309, No. 12, Sep. 22, 1983, pp. 694–698.
Recombinant Aplhal-Antitrypsin Pittsburgh (Met 358-Arg) is a Potent Inhibitor of Plasma Kallikrein and Activated Factor XII Fragment, Chemical Abstracts, vol. 104, No. 15, Apr. 1986, p. 316.
Interaction of Trypsin–Like Enzymes with Small Inhibitors, Chemical Abstracts, vol. 104, No. 7, Feb. 17, 1986, p. 232.
Peptide/Protein Inhibitors of Trypsin and Kallikrein--Primary Structural Requirements, Chemical Abstracts, vol. 99, No. 5, Aug. 1983, p. 237.
Altered Specificaties of Genetically Engineered Alphal-Antitrypsin Variants, Chemical Abstracts, vol. 106, 1987, p. 208.
Modeling Alpha-1-Antitrypsin Function by Protein Engineering, Biological Abstracts, RRM, Resume 30106755.

*Primary Examiner*—Howard E. Schain
*Assistant Examiner*—Susan M. Perkins
*Attorney, Agent, or Firm*—Cushman, Darby & Cushman

[57] ABSTRACT

The invention relates to the variant of human alpha$_1$-antitrypsin of formula:

$$(Ala^{357}, Arg^{358})\ alpha_1\text{-AT}.$$

This compound is useful as a kallikrein inhibitor.

4 Claims, 2 Drawing Sheets

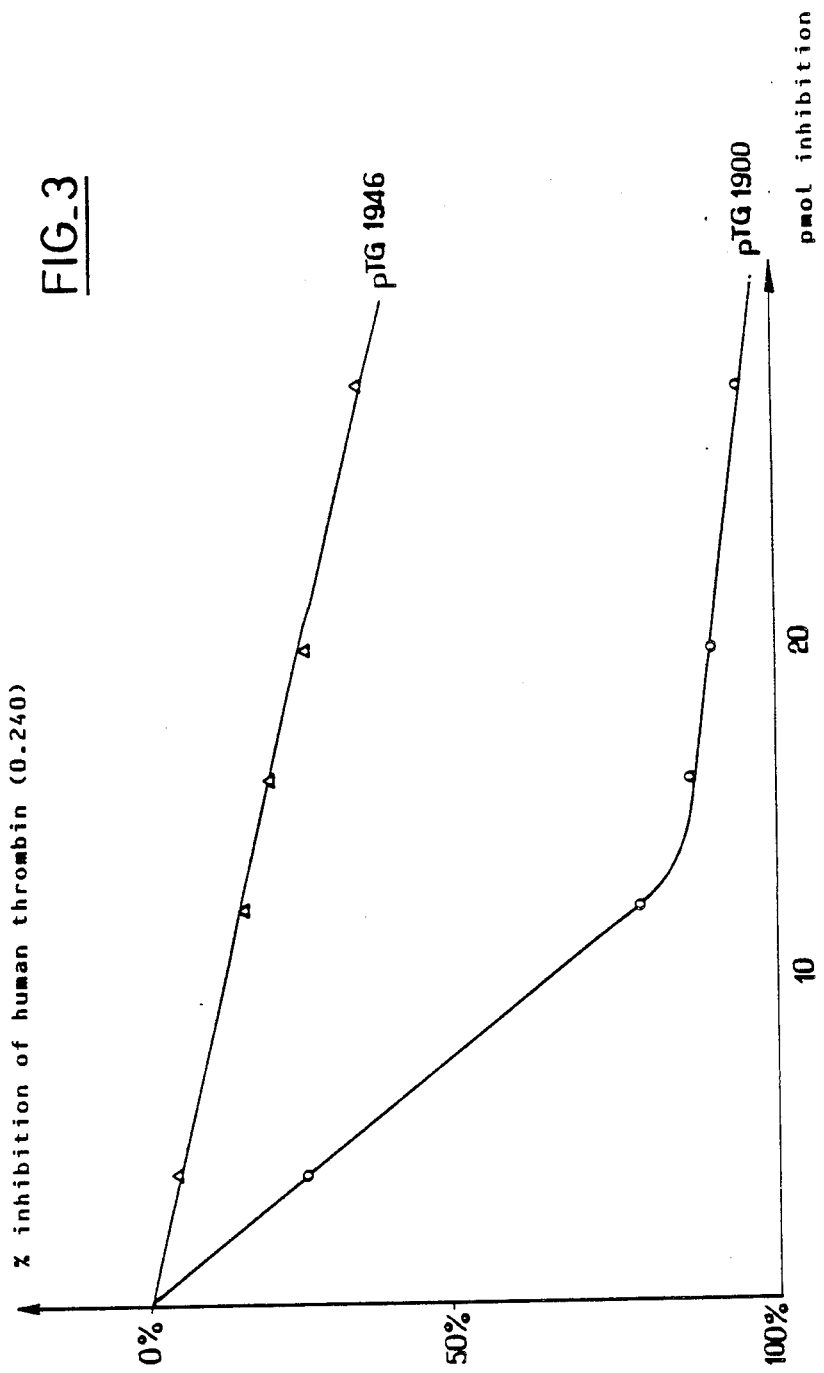

VARIANTS OF ALPHA 1-ANTITRYPSIN WHICH ARE USEFUL, IN PARTICULAR, AS KALLIKREIN INHIBITORS

The present invention relates to a new variant of human alpha$_1$-antitrypsin.

Different variants of human alpha$_1$-antitrypsin have already been described, in particular in patent application No. WO 86/00,337.

The main function of alpha$_1$-antitrypsin (alpha$_1$-AT) is the inhibition of neutrophil elastase in the lungs.

Alpha$_1$-AT plays no part in vivo in the regulation of the coagulation protease, thrombin, nor in that of the phase contact proteases, factor XII and kallikrein.

However, substitution of the Met radical at position P1 of the reactive center of (Met$^{358}$)alpha$_1$-AT by an arginine leads to an effective inhibition of these proteases, thereby demonstrating the critical part played by the radical at P1 in the specific inhibition.

It has been possible, in addition, to demonstrate that the radical at P2 (position 357 of alpha$_1$-AT) is also important; in the first place, for maintaining an appropriate conformation of the reactive centers, and then as an influence on the inhibition properties.

For example, antithrombin III (ATIII), which is a specific inhibitor of thrombin in vivo, has an Arg radical (preferred cleavage site for thrombin) at position P1 and a Gly radical at position P2. C1 inhibitor, which is a predominant inhibitor of kallikrein and of factor XII, also has an arginine radical at position P1 but an Ala radical at position P2. C1 inhibitor is, in vivo, relatively ineffective with respect to thrombin, which possibly reflects a smaller active site size in the case of this enzyme.

The subject of the present invention is a new variant of human alpha$_1$-AT in which the P1 and P2 sites have been modified in an effort to limit the size of the target on this variant.

The invention relates to a variant at position 357 of human alpha$_1$-AT or of (deltaGlu$^1 \rightarrow$Gly$^5$)alpha$_1$-AT.

By replacing the proline at position 357 by an Ala radical, the reactive center of C1 inhibitor is recreated and the inhibitor variant is directed towards kallikrein instead of thrombin.

Thus, the present invention relates, more especially, to a new variant (Ala$^{357}$,Arg$^{358}$)alpha$_1$-AT by way of a kallikrein inhibitor, and which can be used by way of a medicinal product as will be described below.

However, the invention also relates to the (Ala$^{357}$) variants of the different variants described in patent No. WO 86 00337, in particular (Ala$^{357}$) (deltaGlu$^1 \rightarrow$Gly$^5$)alpha$_1$-AT, as well as the corresponding variants in position 358, (Gly$^{358}$), (Ala$^{358}$), (Ile$^{358}$), (Val$^{1358}$), (Leu$^{358}$) and (Phe$^{358}$).

The invention relates to the variants in both their glycosylated and unglycosylated form.

Kallikrein is a serum protease which is involved both in the initiation of coagulation and in fibrinolysis. It is also responsible for the cleavage, from the kininogen of bradykinin, which is a very active oligopeptide which plays an essential part in various processes, in particular inflammatory processes, and in the response to pain.

It has also been shown that bradykinin could participate in the regulation of blood pressure.

C1 inhibitor is the main plasma inhibitor of kallikrein. A deficiency of this inhibitor leads to an unregulated activation of prekallikrein and of factor XII, which leads to a hereditary angioneurotic edema.

As has been shown in the patent mentioned above, (Arg$^{358}$)alpha$_1$-AT is more effective than C1 inhibitor in the inactivation of both kallikrein (activity 4.1 times as great) and factor XIIF (activity 11.5 times as high). For this reason, the protein (Arg$^{358}$)alpha$_1$-AT appears to have the characteristics of a product for the treatment of hereditary angioedema. However, this molecule also has a very substantial antithrombin activity, and it can be advantageous, in some cases, to have different variants which possess a more specific mode of action; this is what is proposed in the context of the present invention.

The new variant (Ala$^{357}$,Arg$^{358}$)alpha$_1$-AT possesses a very much improved kallikrein-inhibiting activity while possessing, on the other hand, very weak antithrombin properties.

Such a product may be used by way of a kallikrein-inhibiting medicinal product, for example for a replacement therapy for deficiencies of C1 inhibitor. It is also possible to envisage its use in the treatment of septic shock and also for the regulation of blood pressure and the treatment of hypertension.

The examples below are designed, more especially, to illustrate other advantages and characteristics of the present invention without, however, in any way limiting its scope.

EXAMPLE 1

EXPRESSION OF MODIFIED ALPHA$_1$-AT IN E. COLI

The plasmids and genetic materials used in these constructions have already been described in the patent application mentioned above.

MUTAGENESIS OF THE HUMAN ALPHA$_1$-AT GENE

The replacement of the Met$^{358}$ residue of alpha$_1$-AT by arginine and of the Pro$^{357}$ residue by Ala was performed by direct mutagenesis using oligonucleotides.

The cloned alpha$_1$-AT cDNA was subcloned in the vector M13, and the DNA of the single-stranded phage was used as a model for a synthetic complementary oligonucleotide containing the desired modification (5' GATAGACCTAGCTATG-GCC 3'). The second strand is synthesized using Klenow polymerase, a transformation is then performed and the plaques containing the mutated gene are identified by screening using the oligonucleotide.

The mutations are confirmed by direct sequencing.

| original sequence | Ala | Ile | Pro | Met | Ser | Ile |
|---|---|---|---|---|---|---|
| | GCC | ATA | CCC | ATG | TCT | ATC |
| mutated sequence | Ala | Ile | Ala | Arg | Ser | Ile |
| | GCC | ATA | GCT | AGG | TCT | ATC |

This technology has been described in detail in the patent mentioned above.

The fragment of the alpha$_1$-AT variant is then introduced into plasmid pTG983 as was described in the previous patent.

A plasmid designated pTG1946 is thereby obtained, which is identical to plasmid pTG983 with the exception of the alpha$_1$-AT gene which has been modified in position 357 and 358.

In that which follows, the plasmids used are the following:

pTG983 (unmodified alpha$_1$-AT)
pTG1900 (Arg$^{358}$ alpha$_1$-AT)
pTG1946 (Ala$^{357}$ Arg$^{358}$ alpha$_1$-AT).

EXPRESSION OF THE MODIFIED ALPHA$_1$-AT IN E. COLI

The variant according to the present invention, obtained by fermentation of E. coli bacteria transformed by pTG1946, was compared with pTG983 and pTG1900.

Clarified sonicated extracts were prepared from induced cultures of E. coli TGE900 containing one of the above three plasmids.

Aliquots of extracts are tested for their capacity to inhibit human neutrophil elastase (this technique having already been described).

The inhibition curves seen in FIG. 1 show that, compared with normal alpha$_1$-AT (Met$^{358}$alpha$_1$-AT), the variant according to the present invention (Ala$^{357}$, Arg$^{358}$)alpha$_1$-AT is incapable of inhibiting neutrophil elastase.

The antikallikrein activity is assessed by measuring at 410 nm the residual extent of hydrolysis of chromosyme PK (benzoyl-Pro-Pre-Arg-4-nitroanilide acetate, Boehringer Mannheim).

2.6 pmol of human plasma kallikrein are preincubated at 37° C. with an increasing amount of inhibitor in 0.1 M Na phosphate/0.15 M NaCl buffer. After 30 minutes, the reaction is stopped by adding 900 μmol of substrate (final concentration 0.5 mM) and the residual enzyme activity is determined.

Figure 2:
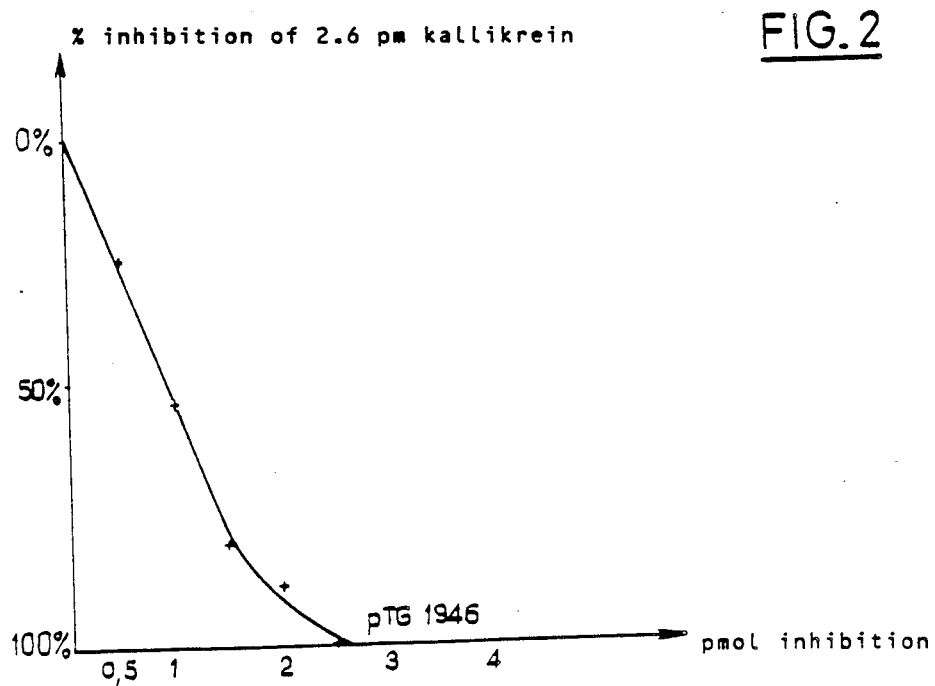

FIG. 2 shows that the variant (Ala$^{357}$, Arg$^{358}$) alpha$_1$-AT is capable of rapidly inhibiting kallikrein. The inhibition curves for thrombin (FIG. 3) and the comparison with alpha$_1$-AT(Arg$^{358}$) show that the variant (Ala$^{357}$,Arg$^{358}$)alpha$_1$-AT inhibits human thrombin only very weakly.

The compound according to the invention can hence be used in a replacement therapy for C1 inhibitor.

Using the technique described above and the methods described in patent No. WO 86/00,337, the other claimed variants are obtained.

The following strain was deposited at the Collection Nationale de Cultures de Microorganismes (National Collection of Microorganism Cultures) of the Institut Pasteur, 28 rue du Docteur-Roux, 75724 PARIS CEDEX 15: E. coli strain TGE900 pTG1946 on 6th June 1986 under No. I-560.

We claim:

1. A variant of human alpha$_1$-AT of formula:

(Ala$^{357}$, Arg$^{358}$) alpha$_1$-AT.

2. The variant as claimed in claim 1 having activity of inhibiting kallikrein.

3. A variant of human alpha$_1$-AT formula: N-terminally deleted (Ala$^{357}$, Arg$^{358}$) human alpha$_1$-AT, said variant being truncated by the 5 amino acids Glu$^1$ to Gly$^5$.

4. The variant as claimed in claim 3, having activity of inhibiting kallikrein.

* * * * *